(12) United States Patent
Payne et al.

(10) Patent No.: US 10,576,201 B2
(45) Date of Patent: Mar. 3, 2020

(54) DUAL LATCHING MICROVALVES

(71) Applicant: SFC Fluidics, Inc., Fayetteville, AR (US)

(72) Inventors: Forrest W. Payne, Fayetteville, AR (US); Greg Lamps, Smyrna, GA (US); Champak Das, Fayetteville, AR (US); Sai Kumar, Johns Creek, GA (US); Ashley Shemain, Flowery Branch, GA (US)

(73) Assignee: SFC Fluidics, Inc., Fayetteville, AR (US)

( * ) Notice: Subject to any disclaimer, the term of this patent is extended or adjusted under 35 U.S.C. 154(b) by 323 days.

(21) Appl. No.: 15/503,310

(22) PCT Filed: Aug. 14, 2015

(86) PCT No.: PCT/US2015/045251
§ 371 (c)(1),
(2) Date: Feb. 10, 2017

(87) PCT Pub. No.: WO2014/036112
PCT Pub. Date: Mar. 6, 2014

(65) Prior Publication Data
US 2017/0224918 A1 Aug. 10, 2017

Related U.S. Application Data

(60) Provisional application No. 62/037,474, filed on Aug. 14, 2014.

(51) Int. Cl.
*A61M 5/168* (2006.01)
*F16K 7/04* (2006.01)
(Continued)

(52) U.S. Cl.
CPC .... *A61M 5/16813* (2013.01); *A61M 5/14212* (2013.01); *A61M 39/227* (2013.01);
(Continued)

(58) Field of Classification Search
CPC ........ F16K 7/045; F16K 7/063; F16K 11/207; F16K 11/205; F16K 11/22; F16K 11/02;
(Continued)

(56) References Cited

U.S. PATENT DOCUMENTS 4,061,142 A * 12/1977 Tuttle .................. A61M 1/30
604/34
4,259,985 A 4/1981 Bergmann
(Continued)

FOREIGN PATENT DOCUMENTS

DE 10 2011 120105 A1 6/2013
JP S60 73176 4/1985
(Continued)

OTHER PUBLICATIONS

Extended European search report for Application No. 15831959.0 (dated Mar. 1, 2018).

*Primary Examiner* — Kevin C Sirmons
*Assistant Examiner* — Alexandra Lalonde

(57) ABSTRACT

A valve for use in connection with microfluidic devices includes a safety feature such that flow is controlled even in the case of a loss of power, thus having applications in critical applications such as the precise delivery of drugs overtime. The valve may be used in connection with multiple tubes delivering drugs, and may be used with a pump, such as an electrochemical pump, to provide the force to move the fluids containing drugs for delivery. In certain applications, more than one medicine may be delivered and metered independently using a single pump with multiple reservoirs and valves.

11 Claims, 6 Drawing Sheets

(51) Int. Cl.
*F16K 99/00* (2006.01)
*F16K 11/02* (2006.01)
*F16K 11/20* (2006.01)
*A61M 5/142* (2006.01)
*F16K 31/02* (2006.01)
*A61M 39/22* (2006.01)
*F16K 17/36* (2006.01)
*F16K 31/00* (2006.01)
*A61M 39/28* (2006.01)

(52) U.S. Cl.
CPC .............. F16K 7/045 (2013.01); F16K 11/027 (2013.01); F16K 11/205 (2013.01); F16K 17/36 (2013.01); F16K 31/002 (2013.01); F16K 31/025 (2013.01); F16K 99/0026 (2013.01); F16K 99/0038 (2013.01); F16K 99/0044 (2013.01); A61M 39/28 (2013.01); *F16K 2099/0069* (2013.01); *F16K 2099/0071* (2013.01); *F16K 2099/0086* (2013.01)

(58) Field of Classification Search
CPC ........ F16K 11/06; F16K 11/24; F16K 31/002; F16K 31/025; F16K 31/082; F16K 99/0038; F16K 2099/0086; F16K 2099/0069; F16K 2099/0071; A61M 5/16813; A61M 5/168; A61M 5/16804; A61M 5/14212; A61M 5/142; A61M 5/14; A61M 5/16881; A61M 5/16827; A61M 39/227; A61M 39/228; A61M 39/22; A61M 39/28; A61M 39/281; A61M 39/284; A61M 39/287; A61M 39/285; A61M 39/286; Y10T 137/87096; Y10T 137/87113

See application file for complete search history.

(56) References Cited

U.S. PATENT DOCUMENTS

| 5,529,281 | A | * | 6/1996 | Brudnicki | F16K 1/123 251/129.03 |
|---|---|---|---|---|---|
| 5,994,816 | A | | 11/1999 | Dhuler | |
| 6,742,761 | B2 | | 6/2004 | Johnson et al. | |
| 6,840,257 | B2 | | 1/2005 | Dario et al. | |
| 6,843,465 | B1 | | 1/2005 | Scott | |
| 7,260,932 | B1 | | 8/2007 | Klimowicz | |
| 8,499,779 | B2 | | 8/2013 | Gillespie | |
| 2002/0087120 | A1 | | 7/2002 | Rogers et al. | |
| 2007/0204612 | A1 | * | 9/2007 | Klimowicz | F16K 7/045 60/527 |
| 2008/0095649 | A1 | | 4/2008 | Ben-Shalom et al. | |
| 2012/0053557 | A1 | | 3/2012 | Abal | |
| 2013/0039779 | A1 | | 2/2013 | Bahar et al. | |
| 2013/0118619 | A1 | * | 5/2013 | Loth | A61M 37/0076 137/625 |

FOREIGN PATENT DOCUMENTS

| WO | 2009149137 A1 | 12/2009 |
|---|---|---|
| WO | 2014036112 A1 | 3/2014 |

* cited by examiner

DUAL LATCHING MICROVALVES

CROSS-REFERENCE TO RELATED APPLICATIONS

This application claims the benefit of U.S. provisional patent application No. 62/037,474, filed on Aug. 14, 2014, and entitled "Multifunctional Microvalves." Such application is incorporated herein by reference in its entirety.

BACKGROUND

The field of the invention is valves for microfluidic applications, and in particular to the use of such microvalves for safe and controlled delivery of fluids from a reservoir.

Fluidic microvalves can be constructed from shape-memory alloys. For example, U.S. Pat. No. 7,260,932 teaches a fluid control pinch valve using shape memory alloy that receives a current to open or close the pinch valve. Similarly, U.S. Pat. No. 6,843,465 teaches a shape-memory wire actuated control valve, in which the shape-memory wire is connected to an electrical platform and mechanically coupled to a transfer mechanism. The actuator is actuated by conducting electrical current through the shape-memory wire causing the wire to contract and thereby actuating the transfer mechanism, which is operably coupled to the fluid control valve such that actuating and de-actuating the transfer mechanism opens and closes the valve. U.S. Pat. No. 6,742,761 teaches a poppet valve that is used for opening and closing a miniature latching valve by means of an actuator mechanism that includes a shape-memory alloy wire. The change in shape of the shape-memory alloy wire causes the poppet to either move toward or away from the valve seat, thereby either closing or opening the valve. U.S. Pat. No. 6,840,257 teaches a proportional valve using a shape-memory alloy actuator, with a shutter axially movable from and towards a valve seat under the control of a shape-memory alloy actuating member.

Valves are a critical component of microfluidic systems. Miniaturized valves can be used in combination with miniaturized pumps to deliver pulsed and/or constant flow of microliter or nanoliter volumes of solution (or less). The valves themselves must be small and use little power to activate. Additional power can be saved by using a latching valve that does not require power to remain in any one state. Latching valves are not designed in a normally open or normally closed state; rather they can rest in either state. In drug delivery and other applications, latching valves are an important safety feature when properly configured as they prevent a direct flow path from a large reservoir to a patient in the case of a system failure.

BRIEF SUMMARY

The present invention relates generally to a valve and systems for using valves for controlled delivery of fluid and to provide a failsafe whereby the state of the valve is maintained despite a loss of power or other failure. This provides, in certain embodiments, certain advantages in applications such as the precise delivery of medicines to a patient over time. In certain embodiments, the valve may be used in connection with multiple tubes delivering drugs, and may be used with a pump, such as an electrochemical pump, to move the fluids containing drugs for delivery. In certain applications, more than one medicine may be delivered and metered independently using a single pump with multiple reservoirs and valves.

These and other features, objects and advantages of the disclosed subject matter will become better understood from a consideration of the following detailed description, drawings, and claims directed to the invention. This brief summary and the following detailed description and drawings are exemplary only, and are intended to provide further explanation of various implementations without limiting the scope of the invention as set forth in the claims.

DETAILED DESCRIPTION

Figure 1A:
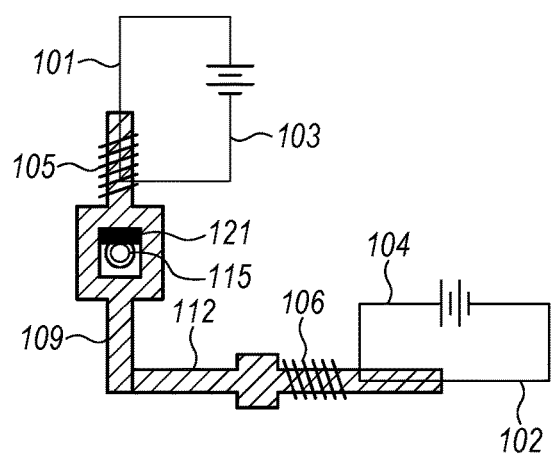
FIG. 1 is a schematic diagram of a single sliding latching nitinol valve in the open (a) and closed (b) position (based on prior art U.S. Pat. No. 7,260,932 B1).
Figure 1B:
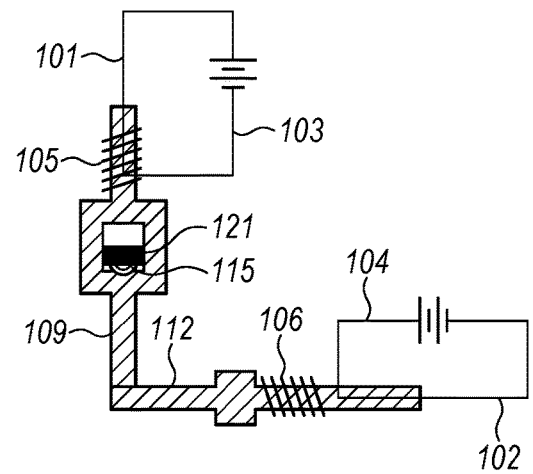

Referring now to FIG. 1 (based on prior art U.S. Pat. No. 7,260,932 B1), a single sliding latching nitinol valve is shown in the open (FIG. 1(a)) and closed (FIG. 1(b)) positions. Tube 115 is located in an open receiving area between valve arm 109 and valve seat 121 which is in a fixed position. To close the valve, nitinol wire 101 attached to valve arm 109 is activated by associated circuit 103 to pull valve arm 109, which thereby pinches tube 115 closed, as shown in FIG. 1(b). A resilient member such as spring 106 on latch arm 112 pushes the latch arm 112 so that it interferes with the return of valve arm 109, causing tube 115 to remain pinched and closed without any additional power requirement. To open the valve, current is applied to circuit 104, which activates nitinol wire 102 attached to latch arm 112. Spring 105 forces valve arm 109 to its open position, where it interferes with the return path of latch arm 112 so that the valve remains open without any additional power. In this way, a single sliding valve may be employed using shape-memory alloy wire that stays in a desired position for an indefinite period of time without the addition of external power, until the valve is moved from the closed to open position, or the open to closed position. The valve is not dependent upon the presence of electrical power once set in either position. In a drug delivery device comprising a reciprocating pump, two of these valves may be used, one as an inlet valve and one as an outlet valve. In this case, there are no restrictions on whether either valve is open or closed so that at any point in time both valves could be open, both valves could be closed or one could be open while the other was closed. If both valves are open due to a system failure then there would be an open path from the reservoir to the delivery site, which could have devastating consequences in drug delivery applications.

Figure 2:
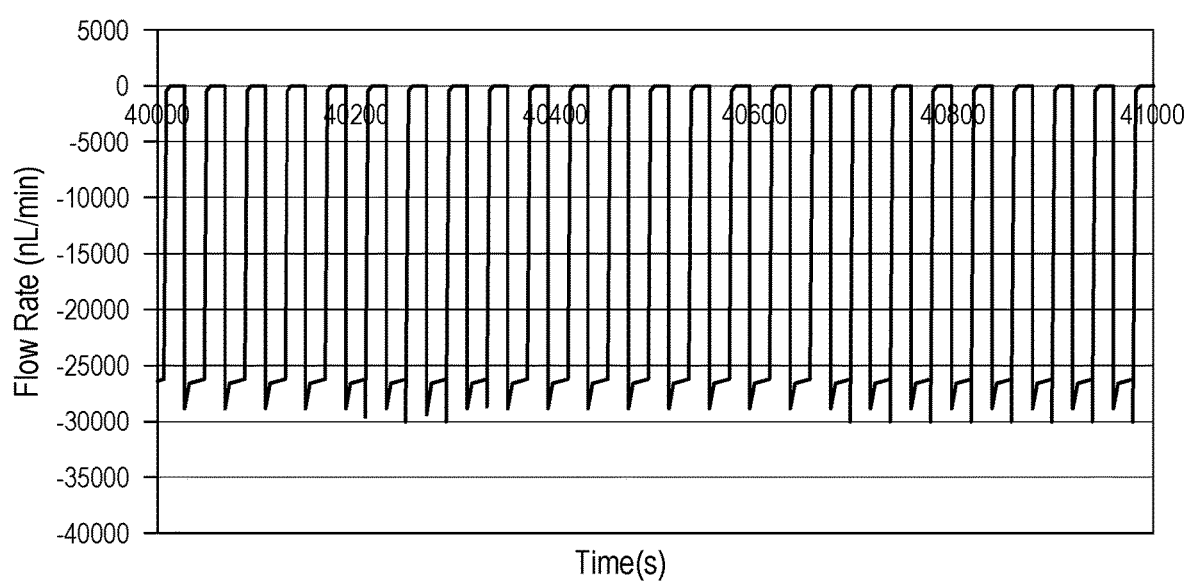
FIG. 2 is a graph showing fluid flow through a fluid sensor as the single sliding latching nitinol valve of FIG. 1 opens and closes.

The graph of FIG. 2 shows experimental results from the opening and closing of the valve shown in FIG. 1. As can be seen from FIG. 2, flow through tube 115 is quickly and effectively opened and closed by the operation of the valve.

Figure 3A:
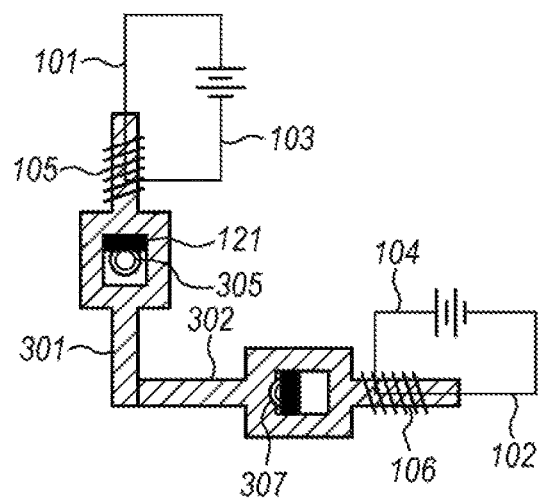
FIG. 3 is a schematic diagram of a dual sliding latching nitinol valve in the inlet open/outlet closed (a) and outlet open/inlet closed (b) position.
Figure 3B:
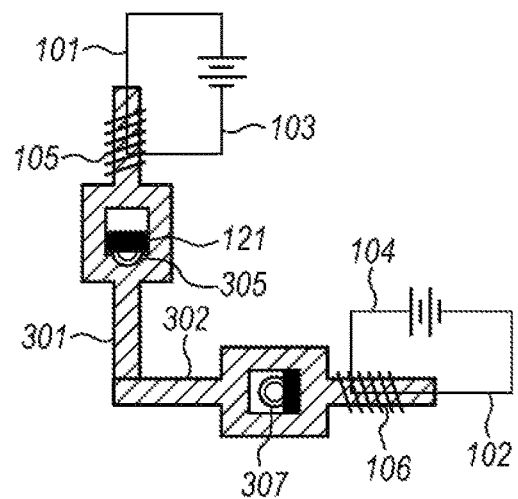

FIG. 3 shows the inventive step beyond the valve of FIG. 1 in which two sections of a single fluid path (or two separate fluid paths), 305 and 307, cannot both be in an open position at the same time. In the configuration of FIG. 3(a), tube 305 is open while tube 307 is pinched closed. In the configuration of FIG. 3(b), tube 305 is pinched closed while tube 307 is open. The dual sliding latching nitinol valve of FIG. 3 is designed so that both valves close during switching states and it is mechanically impossible for both tubes 305 and 307 to be open at the same time, thereby always preventing an unintended flow of fluid through the system in the case of a failure.

To move from the configuration of FIG. 3(a) to the configuration of FIG. 3(b), nitinol wire 101 attached to inlet valve arm 301 is activated by running current through associated circuit 103. This causes valve arm 301 to move up, pinching inlet tube 305 and allowing spring 106 to force outlet valve arm 302 to a position where outlet tube 307 is open and inlet valve arm 301 is prevented from returning to its original position. To return to the configuration of FIG. 3(a), nitinol wire 102 attached to outlet valve arm 302 is activated by running a current through associated circuit 104. This causes outlet valve arm 302 to move to the right as shown in the figure, thereby pinching outlet tube 307 closed and allowing spring 105 to force inlet valve arm 301 to a position where inlet tube 305 is open and outlet valve arm 302 is prevented from returning to its open position. It may be seen that during each transition, there is a brief period during which both inlet tube 305 and outlet tube 307 are both closed; however, there is no time when both inlet tube 305 and outlet tube 307 are open, as this operation is mechanically prevented. This arrangement prevents flow in the case of a failure, such as is vitally important when the valve is used for the delivery of medication from a reservoir to a patient.

Figure 4:
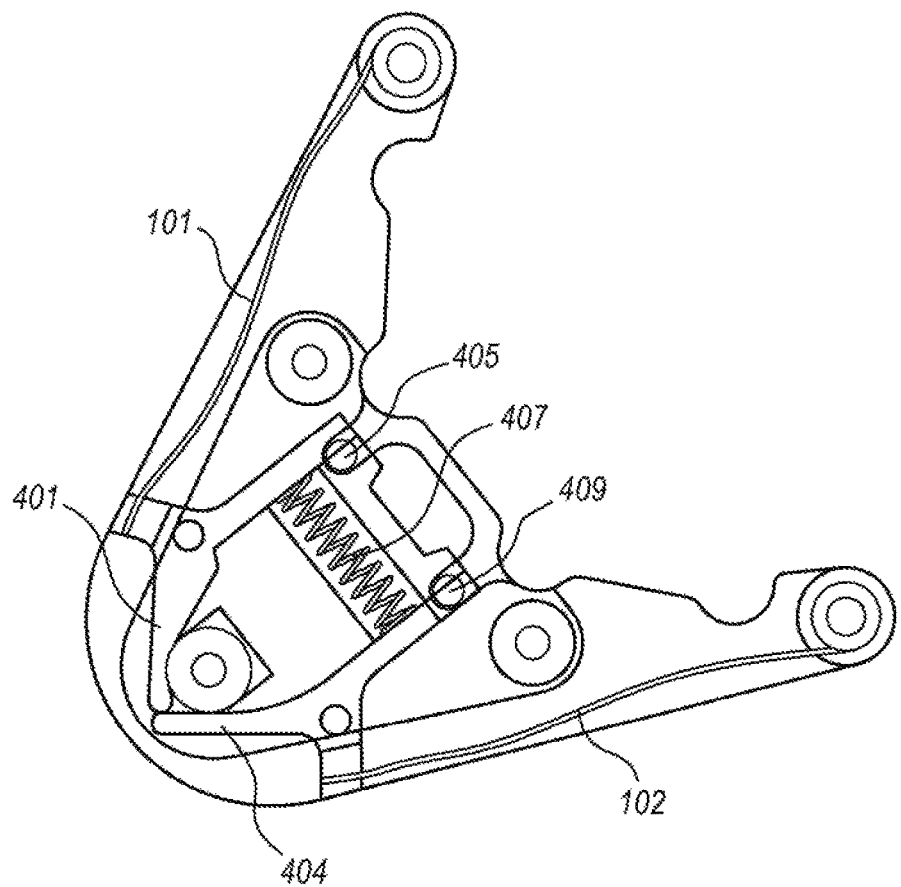
FIG. 4 is a schematic diagram of a dual pivot latching nitinol valve.

FIG. 4 depicts a variation on this design using a dual pivot latching nitinol valve. The figure shows the position of outlet tube 409 pinched closed by outlet valve arm 404. To change the valve position, nitinol wire 101 attached to inlet arm 401 is activated to move inlet arm 401 to pinch inlet tube 405. During this time, spring 407 forces outlet arm 404 to move so that outlet tube 409 is open (inlet tube 405 is closed) and outlet arm 404 prevents inlet arm 401 from returning to its normal position. Later activation of nitinol wire 102 attached to outlet arm 404 returns the valve to the open position (inlet tube 405 is open and outlet tube 409 is closed) as shown in FIG. 4. As with the arrangement depicted in FIG. 3, it may be seen that at no time in the process are both tubes 405 and 409 open. Such operation is mechanically prevented by the design of the valve, thereby providing a safety mechanism in the case of valve failure. The use of a pivot arm allows for a mechanical advantage to be used to reduce the length of nitinol wires 101 and 102 required to switch valve positions. The result is thus a smaller and more energy efficient valve.

Although various embodiments of the invention have been described herein with reference to particular applications related to the delivery of fluids and in particular drugs, it will be apparent that the invention is not so limited. In addition, the dual valve safety mechanism can be realized with a ratcheting action, or an appropriately shaped cam, for example. Furthermore, any actuation mechanism can be used to switch valve states of coupled valves including solenoid, magnetic, pneumatic or hydraulic controls, stepping motor, or manual operation. In addition, the preceding description has focused on two-dimensional layouts of the sliding or pivoting members, however, it can be extended to acting members which are arranged in a non-planar manner. Larger or smaller embodiments of a dual latching valve could be used for safety-enhanced flow control at any scale.

Figure 5:
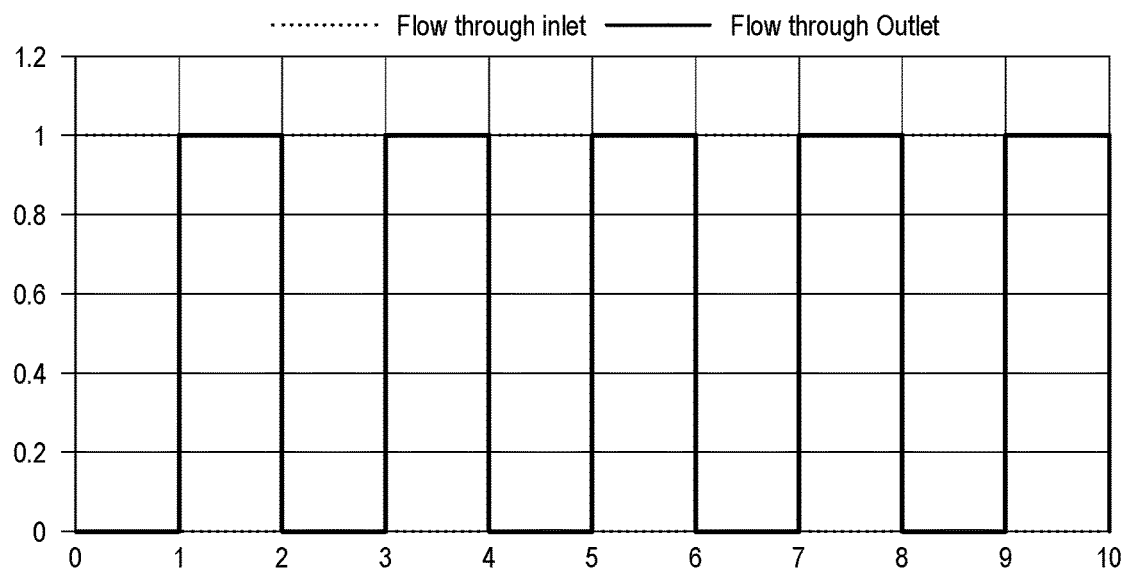
FIG. 5 is a graph showing fluid flow through the dual pivot latching valve of FIG. 4.

The graph of FIG. 5 shows normalized results from the opening and closing of the dual pivot latching nitinol valve of FIG. 4. As can be seen from FIG. 5, like in FIG. 2, flow through each of outlet tube 409 and inlet tube 405 is efficiently switched by the valve. However, FIG. 5 also shows that the opening of either one of the valves always directly corresponds with the closing of the other. In this graph the y-axis shows no flow at 0 and flow at 1. The x-axis shows the cycles of alternately switching the two valve arms between open and closed. There is no time when fluid is flowing through both of the valves because at no time are both outlet tube 409 and inlet tube 405 open, thereby preventing flow through both simultaneously.

Figure 6:
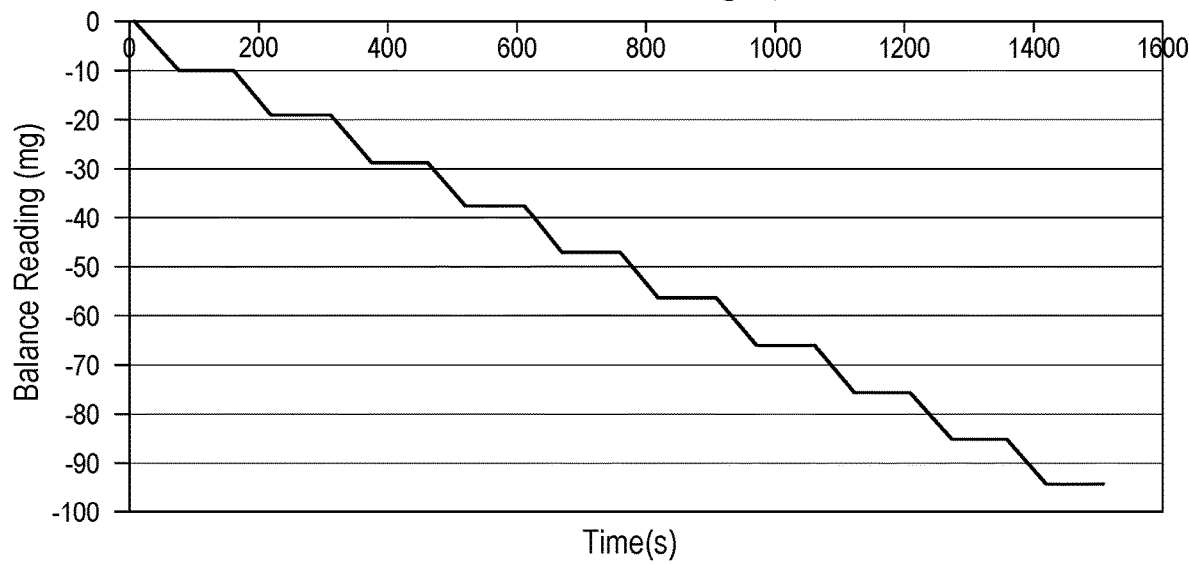
FIG. 6 is a graph showing results of a syringe pump coupled with the dual pivot latching valve of FIG. 4 and delivering it to a pressurized reservoir at 2 psi.

The graph of FIG. 6 shows experimental results of using a syringe pump as a fluid displacement source with the dual pivot latching valve of FIG. 4. Fluid is removed from a balance to provide a weight reading and delivered to a reservoir held at a pressure of 2 psi. As can be seen from FIG. 6, fluid is delivered from the balance in a stair-step fashion, with fluid removal from the balance alternating with a period when the valve is closed and fluid is being delivered to an off-balance reservoir, in a relatively even delivery over time. This data also shows that there is no backflow onto the balance from the pressurized reservoir, illustrating that there is never a time when both valves arms are open.

Figure 7:
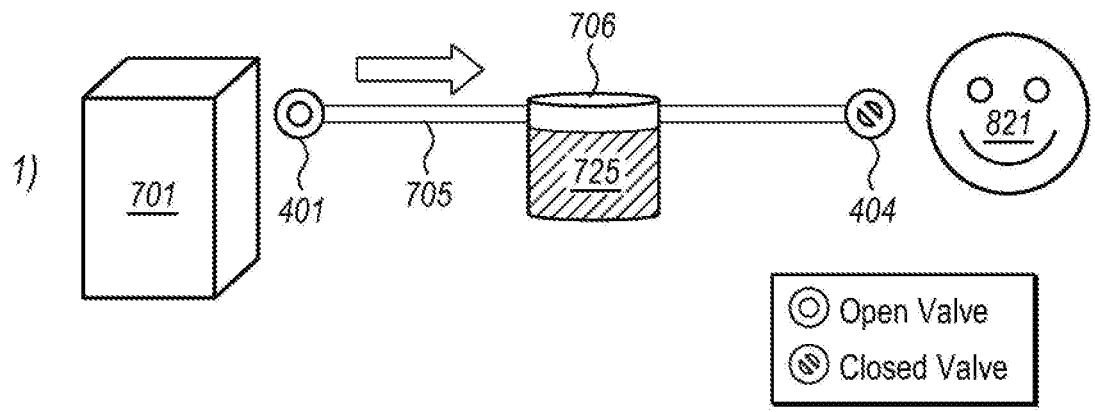
FIG. 7 shows one dual latching valve used to control fluid flow from a reciprocating pump.
Figure 7:
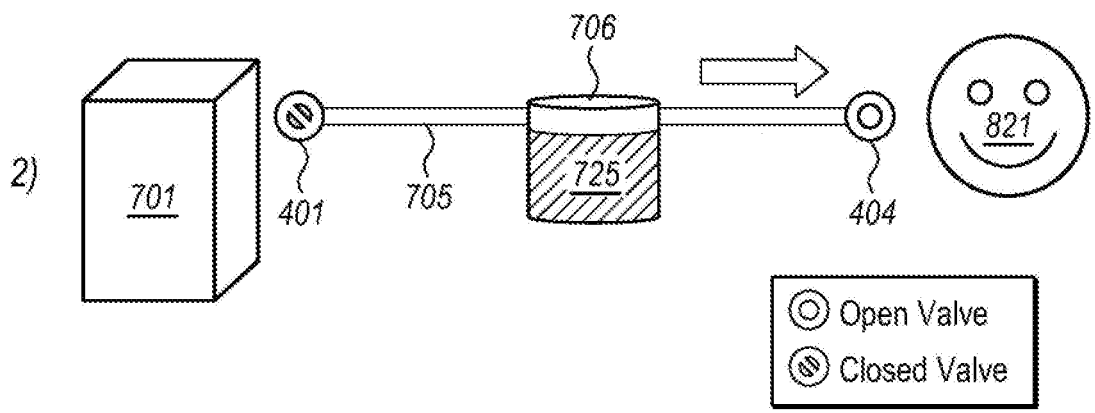

FIG. 7 shows an application of a dual latching valve as described herein with an electrochemical pump or "ePump" 725. Electrochemical pumps suitable for use with the invention are taught, for example, in U.S. Pat. Nos. 7,718,047, 8,343,324, and 8,187,441, which are incorporated by reference herein. In this embodiment a dual latching valve is used for controlled dosing of a fluid, such as a drug to patient 821. In the first step, the inlet valve arm is open (the outlet valve is closed) and the ePump is used to draw a dose of fluid along flow path 705 into chamber 706. In the second step, the outlet valve is open (the inlet valve is closed) and the ePump is used to push fluid from chamber 706 into the patient 821. Please note that at no time is there an open path from the reservoir 701 to the patient, an important safety feature in drug delivery.

Figure 8:
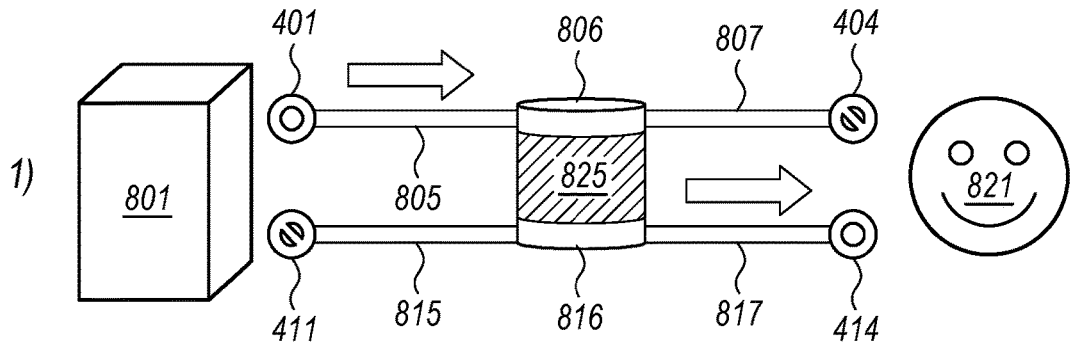
FIG. 8 shows two dual latching valves with a two-sided reciprocating electrochemical pump, showing the two steps in drug delivery.
Figure 8:
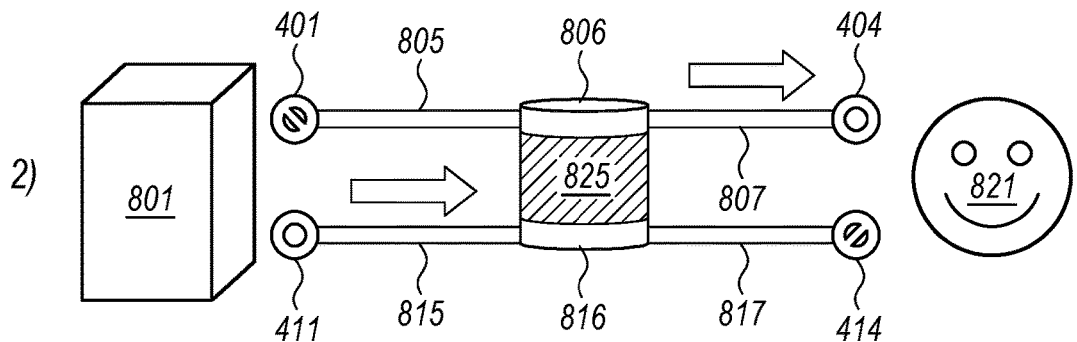

FIG. 8 shows an application of a two-sided ePump 825 used in combination with two dual-latching valves to generate near-continuous controlled dosing of a fluid, such as a drug, to a patient 821. The two-sided ePump 825 has two chambers 806 and 816. As the pump action draws fluid into the top chamber 806, it expels fluid from the bottom chamber 816. Conversely, as fluid is drawn into bottom chamber 816, it is expelled from top chamber 806. As can be seen in FIG. 8, there are two distinct fluid paths that run from the reservoir 801 to patient 821: 805-806-807 and 815-816-817. Flow through each path is controlled by a dual latching valve. The upper dual latching valve has inlet valve arm 401 and outlet valve arm 404 which control flow through path 805-806-807. Just as described in FIG. 4, when inlet valve 401 is open, then outlet valve 404 must be closed. And, when outlet valve 404 is open, then inlet valve 401 must be closed.

This important control and safety feature allows only the delivery of a metered dose (the volume of chamber 806) of fluid to be delivered and prevents the possibility of an open channel running from reservoir 801 to the patient. The same organization of inlet valve 411 and outlet valve 414 controls fluid movement along path 815-816-817.

Alternatively, by arranging the inlet line 805 and outlet line 817 to both run through valve arm 401 and the outlet line 807 and inlet line 815 to both run through valve arm 404, then only one dual latching valve is needed to provide flow from reservoir 801 to the patient 821. In this arrangement as well, at no time is there an open fluid flow path from the reservoir to the patient.

The following steps describe how a metered dose of fluid is delivered in a near continuous fashion from reservoir 801 to the patient. In this case, the system has already been primed so that both fluid paths are full of fluid. In step (1), inlet valve 401 and outlet valve 414 are open and outlet valve 404 and inlet valve 411 are closed. When the ePump 825 is activated, it first pulls fluid from the drug reservoir 801 through flow path 805 and into chamber 806 where it is stored. Simultaneously, ePump 825 expels fluid stored in chamber 816 through path 817 and into the patient. In step (2), the valves are reversed such that output valve 404 and input valve 411 are open and input valve 401 and output valve 414 are closed. In this case, the pump draws fluid from the reservoir 801 through flow path 815 and into chamber 816 where it is stored. Simultaneously, the metered volume of fluid stored in chamber 806 (from step 1) is expelled through flow path 807 into the patient. Repeating of Steps 1 and 2 will result in near continuous (or intermittent) and safe delivery of controlled doses of fluid (in this case, a drug) to the patient.

Figure 9:
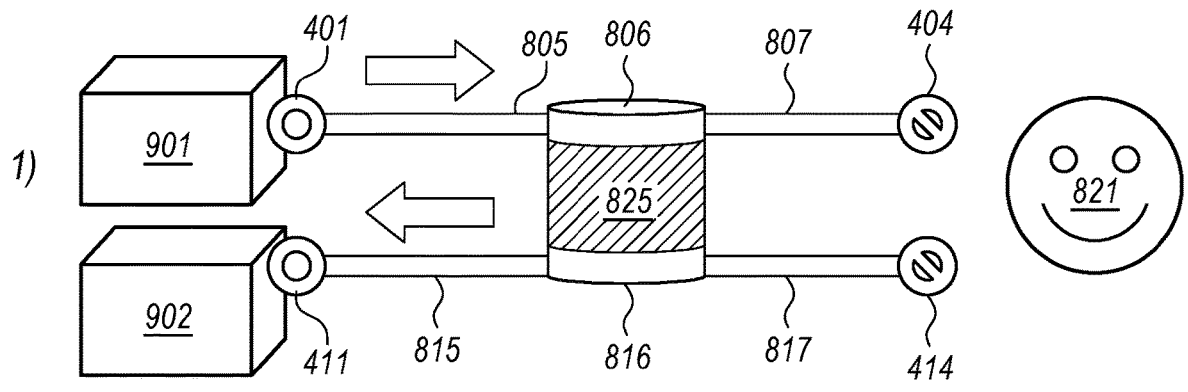
FIG. 9 shows two dual latching valves with two-sided reciprocating electrochemical pump to deliver controlled amounts of two different drugs to a patient.
Figure 9:
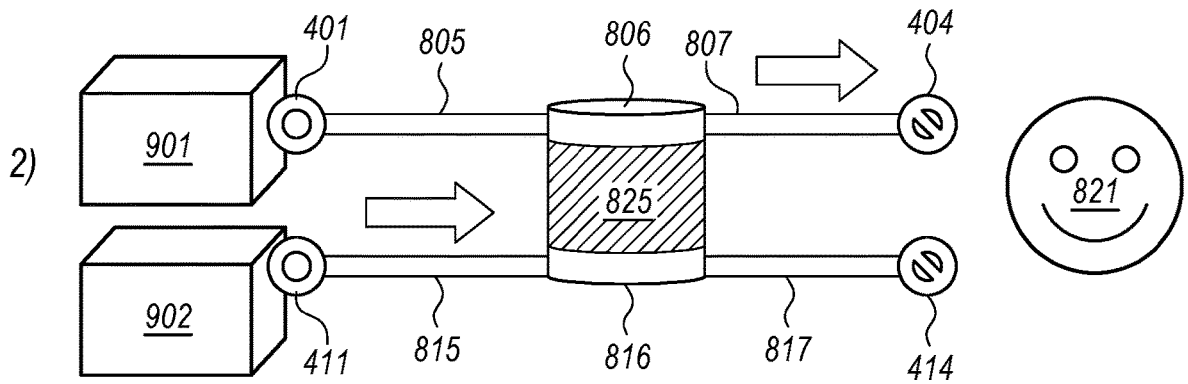

FIG. 9 shows a variation of the arrangement in FIG. 8 wherein two different drugs may be dispensed to a patient 821 from two different reservoirs 901 and 902. Using the steps described in FIG. 8, drug A in reservoir 901 would be delivered in alternation with drug B in reservoir 902. However, it may be desirable to deliver more doses of drug A and fewer doses of drug B. For example, insulin and glucagon as may be used in conjunction for treatment of diabetes, but insulin may need to be dispensed in more volume and or more frequently (or alternatively less) than glucagon. The following steps would allow differential and controlled delivery of two drugs using only one dual-sided ePump and two dual-latching valves. For example, nine doses of drug A in reservoir 901 are needed before a single dose of drug B in reservoir 902 is delivered to the patient. Starting with a fully primed system with both fluid paths 805-806-807 and 815-816-817 filled with the respective fluids: drug A and drug B. In Step 1, inlet valves 401 and 411 are both open and outlet valves 404 and 414 are both closed. The first action of ePump 825 draws a metered amount of fluid from reservoir A into chamber 806 where it is stored. Simultaneously, fluid is expelled from chamber 816 through the only open path: back into reservoir 902. In Step 2, the top dual-latching valve switches positions such that inlet valve 401 is closed and outlet valve 404 is open. This means that the second action of ePump 825 expels the fluid stored in reservoir 806 out through path 807 and into the patient 821. Repeating Steps 1 and 2 results in only fluid from reservoir 901 (drug A) being delivered to the patient, while the fluid from reservoir 902 (drug B) is cycled back and forth between reservoir 902 and chamber 816, this cycling back and forth potentially having a mixing or stirring effect on the contents of the reservoir. Once it is desired to deliver fluid from reservoir 902 to the patient 821 then the bottom dual-latching valve will switch positions such that inlet valve 411 is closed and outlet valve 414 is open so that the fluid stored in chamber 816 is expelled to the patient 821. Opposite protocol to the above would cause repeated delivery of fluid from reservoir B to be delivered to the patient and for fluid from reservoir A to be cycled back and forth between reservoir 901 and chamber 806. By selectively operating the two dual-latching valves, each drug can be selectively pumped back into its originating reservoir or to the patient as needed.

Although various embodiments of the invention has been described herein with reference to particular applications related to the delivery of fluids and in particular drugs, it will be apparent that the invention is not so limited, and instead will find application in other fields where the precise delivery of fluids is desired in a fail-safe manner. Furthermore, although certain embodiments of the invention have been described for use in connection with an ePump, it will be apparent that the invention is not so limited, and that other types of pumps could be used in connection with the valves of the invention as described herein. In addition, although nitinol has been used as the shape-memory alloy in certain embodiments described herein, it will be understood that other shape-memory alloys or materials or actuation methods could be substituted therefor within the scope of the invention.

Unless otherwise stated, all technical and scientific terms used herein have the same meaning as commonly understood by one of ordinary skill in the art to which this invention belongs. Although any systems and materials similar or equivalent to those described herein can also be used in the practice or testing of the present invention, a limited number of the exemplary systems and materials are described herein. It will be apparent to those skilled in the art that many more modifications are possible without departing from the invent concepts herein. All terms used herein should be interpreted in the broadest possible manner consistent with the context. Any ranges expressed herein are intended to include all particular values within the stated range, as well as all sub-ranges that fall within the stated range.

The present invention has been described with reference to the foregoing specific implementations. These implementations are intended to be exemplary only, and not limiting to the full scope of the present invention. Many variations and modifications are possible in view of the above teachings. The invention is intended to be limited only as set forth in the appended claims.

The invention claimed is:

1. A dual latching microvalve, comprising:
   a. a first valve arm comprising a first valve arm end, and further comprising a first valve arm receiving area adapted to receive a compressible first tube;
   b. a first valve seat positioned within the first valve arm receiving area of the first valve arm and adjacent to the first tube to form a first valve;
   c. a second valve arm comprising a second valve arm end, and further comprising a second valve arm receiving area adapted to receive a compressible second tube, and wherein the second valve arm is positioned relative to the first valve arm such that the second valve arm end engages the first valve arm end;
   d. a second valve seat positioned within the second valve arm receiving area and adjacent to the second tube to form a second valve;
   e. a first actuation mechanism attached to the first valve arm;

f. a second actuation mechanism attached to the second valve arm; and g. at least one electrical power source electrically connected in a circuit with one or more of the first actuation mechanism and the second actuation mechanism, wherein the second actuation mechanism is configured to receive a current from the at least one electrical power source that causes the second valve arm to move and allow the first valve arm end to move against the second valve arm end thereby compressing the second tube against the second valve seat within the second valve arm receiving area and holding the second tube in a compressed state and thus closing the second valve, while allowing the first tube to remain in an uncompressed state and thus allowing the first valve to remain open without the addition of further electrical power from the at least one electrical power source, and wherein the first actuation mechanism is configured to receive a current from the at least one electrical power source that causes the first valve arm to move and allow the second valve arm end to slide against the first valve arm end thereby allowing the second tube to remain uncompressed within the second valve arm receiving area and thus allow the second valve to remain open, while compressing the first tube against the first valve seat within the first valve arm receiving area and holding the first tube in a compressed state thereby closing the first valve without the addition of further electrical power from the at least one electrical power source.

2. The dual latching microvalve of claim 1, further comprising:

a. a first resilient member engaged with the first valve arm to bias the first valve arm toward the first valve seat; and b. a second resilient member engaged with the second valve arm to bias the second valve arm toward the second valve seat.

3. The dual latching microvalve of claim 2, wherein the first and second resilient members comprise springs.

4. The dual latching microvalve of claim 1, wherein one or more of the first actuation mechanism and the second actuation mechanism comprise a shape-memory material.

5. The dual latching microvalve of claim 1, wherein both the first valve and second valve are applied to a single flow path through the first and second tubes wherein one of the first and second valves must be closed when the other of the first and second valves is open.

6. The dual latching microvalve of claim 5, further comprising:

a. a reservoir for holding a fluid; and b. a dosing chamber fluidically connected to the reservoir by the first tube, wherein the dual latching microvalve is configured, when the first valve is open and the second valve is closed, to draw the fluid from the reservoir to the dosing chamber, and when the second valve is open and the first valve is closed, to push the fluid from the dosing chamber into a patient.

7. The dual latching microvalve of claim 6, wherein the fluid is a drug, and wherein a maximum volume of the dosing chamber is sized to accommodate the drug being delivered to the patient.

8. The dual latching microvalve of claim 7, wherein the delivery of the drug from the dosing chamber is timed based on an input signal.

9. The dual latching valve of claim 6, wherein the first valve and second valve are configured to create a mixing action between the reservoir and the dosing chamber.

10. The dual latching microvalve of claim 1, wherein the first actuation mechanism and second actuation mechanism are selected from the group consisting of a solenoid, a motor, a pneumatic actuation mechanism, and a hydraulic actuation mechanism.

11. The dual latching microvalve of claim 1, wherein one or more of the first actuation mechanism and the second actuation mechanism comprises a cam or a ratchet.

* * * * *